US00PP19968P2

(12) United States Plant Patent
Verschoor

(10) Patent No.: US PP19,968 P2
(45) Date of Patent: Apr. 28, 2009

(54) ***PHLOX* PLANT NAMED 'PINA COLADA'**

(50) Latin Name: *Phlox paniculata*
Varietal Denomination: Pina Colada

(75) Inventor: Jan Verschoor, Haarlem (NL)

(73) Assignee: Witteman & Co, Hillegom (NL)

( * ) Notice: Subject to any disclaimer, the term of this patent is extended or adjusted under 35 U.S.C. 154(b) by 35 days.

(21) Appl. No.: 11/986,281

(22) Filed: Nov. 20, 2007

(51) Int. Cl.
*A01H 5/00* (2006.01)

(52) U.S. Cl. ..... Plt./320
(58) Field of Classification Search ..... Plt./320
See application file for complete search history.

*Primary Examiner*—S. B McCormick Ewoldt
(74) *Attorney, Agent, or Firm*—Jondle & Associates, P.C.

(57) ABSTRACT

A new *phlox* plant particularly distinguished by having pure white flowers, compact plant habit, healthy foliage and good mildew resistance, is disclosed.

2 Drawing Sheets

Genus and species: *Phlox paniculata.*
Variety denomination: 'Pina Colada'.

BACKGROUND OF THE NEW PLANT

The present invention comprises a new and distinct cultivar of *phlox*, botanically known as *Phlox paniculata,* and hereinafter referred to by the cultivar name 'Pina Colada'. The new cultivar originated from an open pollination in 2005 in Haarlem, The Netherlands between unknown male and female *Phlox paniculata* plants.

The new cultivar was selected from the results of the open pollination in 2006 in Haarlem, The Netherlands and has been asexually reproduced through two generations by vegetative cuttings in Haarlem, The Netherlands since that time. The present invention has been found to retain its distinctive characteristics through successive asexual propagations.

SUMMARY OF THE INVENTION

The following are the most outstanding and distinguishing characteristics of this new cultivar when grown under normal horticultural practices in Haarlem, The Netherlands.

1. Pure white flower color;
2. Compact habit;
3. Healthy foliage; and
4. Good mildew resistance.

DESCRIPTION OF PHOTOGRAPHS

This new *phlox* plant is illustrated by the accompanying photographs which show blooms and foliage of the plant in full color, the colors shown being as true as can be reasonably obtained by conventional photographic procedures. The photographs are of a 1 year-old plant grown in a greenhouse in Haarlem, The Netherlands.

DESCRIPTION OF THE NEW CULTIVAR

Figure 1:
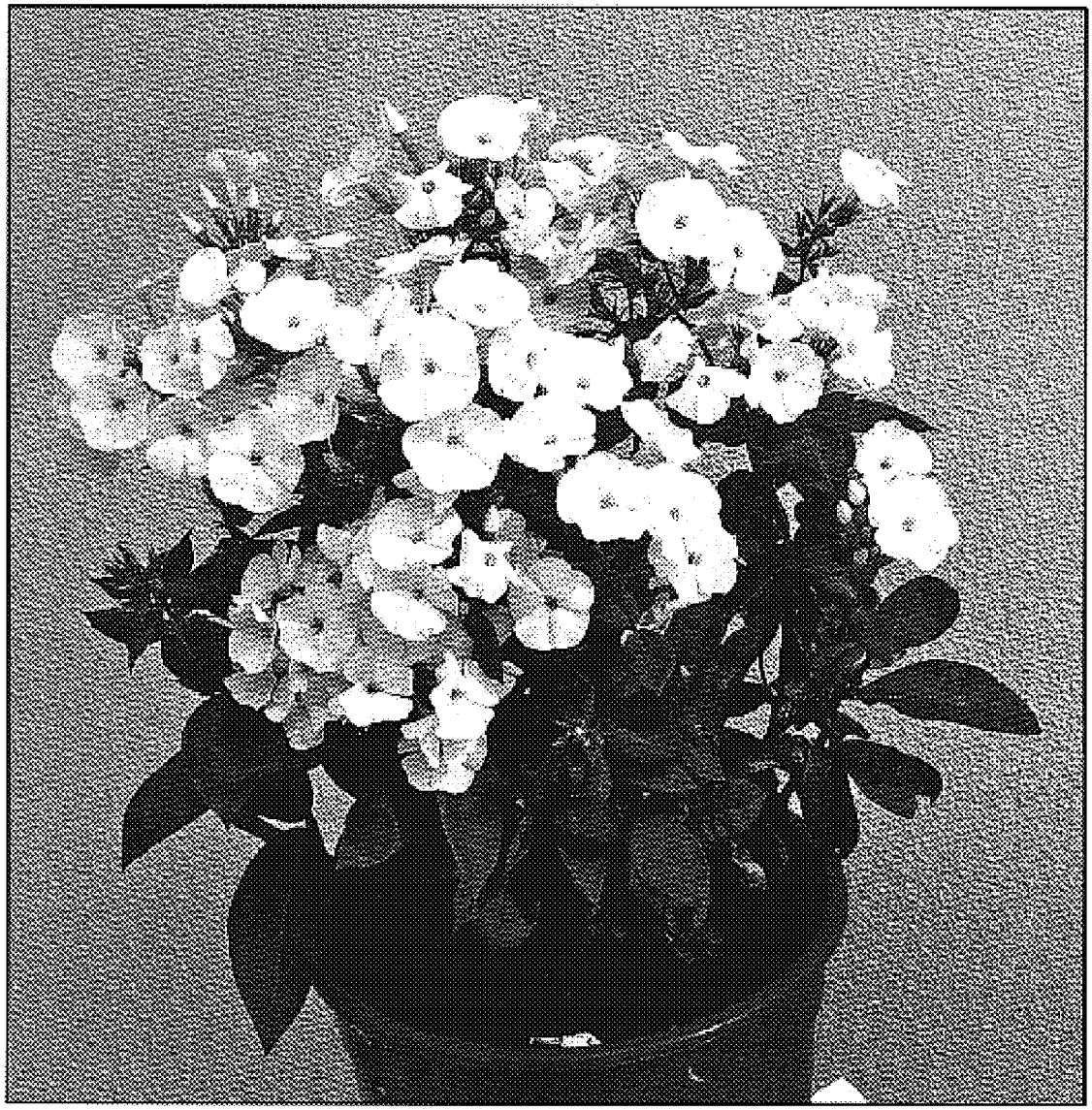
FIG. 1 shows the overall plant habit, including blooms, buds and foliage.
Figure 2:
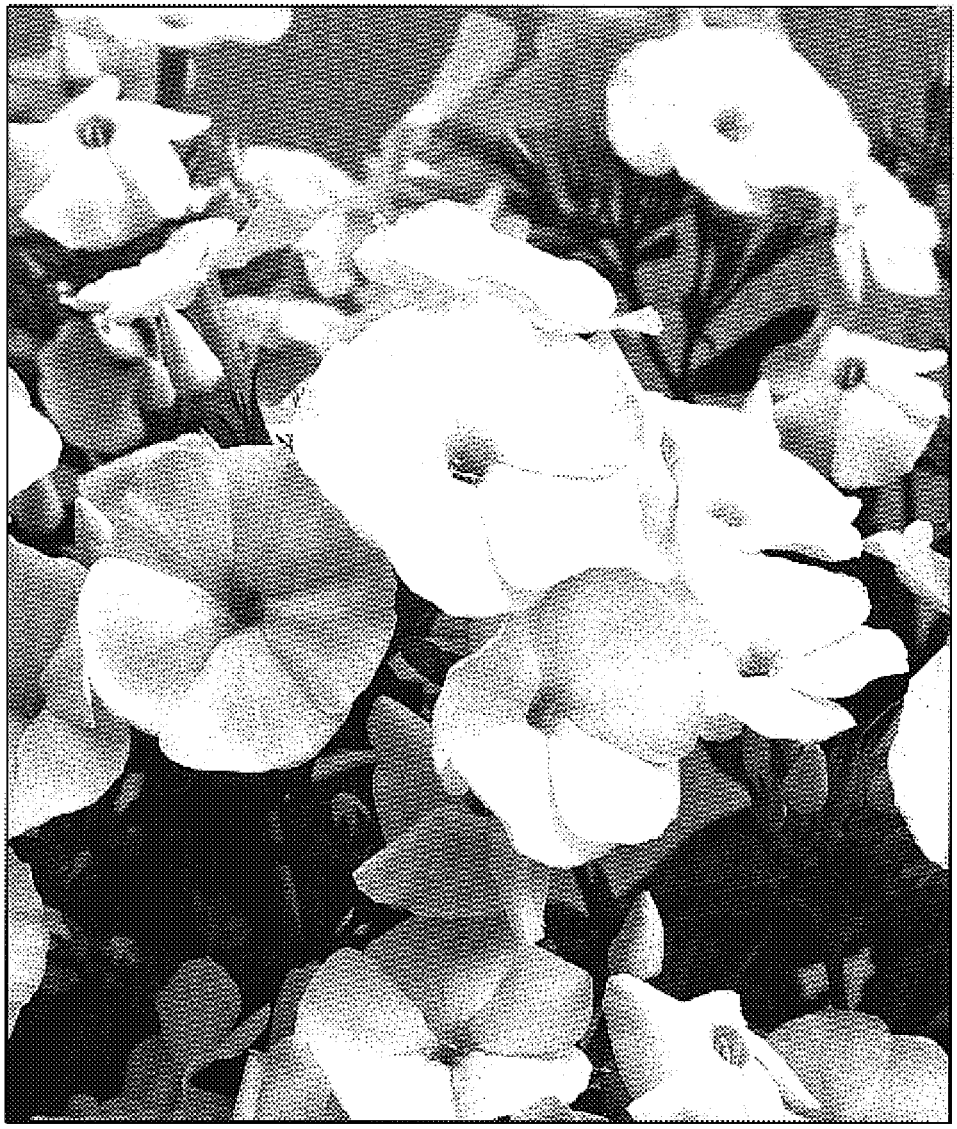
FIG. 2 shows a mature flower.
Figure 3:
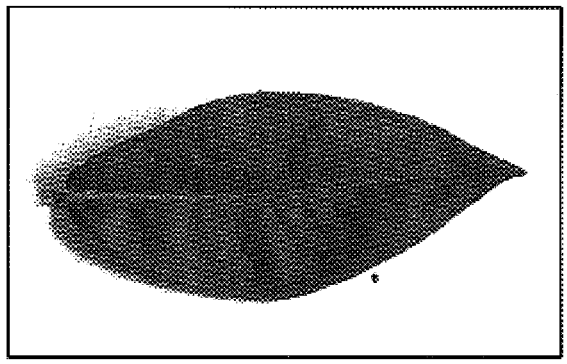
FIG. 3 shows a mature leaf of the plant.

The following detailed description sets forth the distinctive characteristics of 'Pina Colada'. The data which define these characteristics were collected from asexual reproductions carried out in Haarlem, The Netherlands. The plant history was taken in August on 1 year old plants which were planted and grown outdoors in daytime temperatures between 14° and 32° C. and nighttime temperatures between 5° C. and 15° C. No pinchings, growth retardants or photoperiodic treatments were used. Observations were made when the plants were in natural outdoor light. Color reference are primarily to the R.H.S. Colour Chart of The Royal Horticultural Society of London (R.H.S.) (2001).

DETAILED BOTANICAL DESCRIPTION

Classification:
- *Family.*—Polemoniaceae.
- *Botanical.*—*Phlox paniculata.*
- *Common name.*—*Phlox.*

Parentage:
- *Female parent.*—Unknown.
- *Male parent.*—Unknown.

Growth:
- *Form.*—Herbaceous perennial.
- *Habit.*—Upright, moderate to low vigor.
- *Shape.*—Inverted triangle.
- *Height* (*measured from the top of the soil*).—33.6 cm.
- *Diameter.*—22.9 cm.
- *Growth rate.*—10.0 cm per month.
- *Flowering response.*—9 months.
- *Time to produce a finished flowering plant.*—25 weeks from rooted cutting for a 1.5 liter container.
- *High temperature tolerance.*—Tolerant to at least 35° C.
- *Lower temperature tolerance.*—Hardy to at least USDA Zone 4.
- *Root.*—White, thin, fibrous, sparse, freely branching.

Branches:
- *Habit.*—Moderate; basal branching.
- *Number of branches.*—4 flowering stems (the plants have been pinched once at 6.5 cm above soil level).

Stems:
- *Shape/appearance.*—Round, glaborous, slightly glossy.
- *Aspect.*—Rounded.
- *Color.*—RHS 144A (Yellow-green).

*Diameter.*—0.3 cm.
*Stem length* (*excluding inflorescence*).—16.1 cm.
*Internode length.*—2.0 cm.
*Strength.*—Strong.
*Pubescence.*—Absent.

Leaves:
*Arrangement.*—Opposite, single.
*Quantity of leaves* (*per lateral branch*).—16.
*Durability to stress.*—High.
*Shape.*—Elliptic.
*Apex.*—Apiculate.
*Base.*—Obtuse.
*Color* (*mature leaves*).—Upper surface: RHS 137B (Green). Lower surface: RHS 137C (Green).
*Color* (*immature leaves*).—Upper surface: RHS 137A (Green). Lower surface: Between RHS 137C (Green) to RHS 138A (Green).
*Margin.*—Revolute, short, fine serrate (approx. 30 teeth per cm).
*Size.*—Length: 7.3 cm. Width: 3.2 cm.
*Texture* (*upper surface*).—Smooth, glabrous.
*Pubescence.*—Absent.
*Venation.*—Type: Pinnate. Color: Upper surface: Between RHS 144B (Yellow-green) to RHS 144C (Yellow-green). Lower surface: Between RHS 144C (Yellow-green) to RHS 144D (Yellow-green).
*Petiole.*—Shape: V-shaped. Length: 0.20 cm. Width: 0.25 cm. Height: 0.20 cm. Color (Both surfaces): Between RHS 144C (Yellow-green) to RHS 145A (Yellow-green).

Flower Buds:
*Color.*—RHS 157D (Green-white); lower half (immature calyx) RHS 144A (Yellow-green); base RHS 144C (Yellow-green).
*Shape.*—Elliptic to narrow obovate.
*Size.*—Length: 2.3 cm. Diameter: 0.5 cm.
*Rate of opening.*—Open approximately 4 days.

Inflorescence:
*Blooming habit.*—Continuous during natural flowering season.
*Inflorescence type.*—Self-cleaning, compound terminal panicle.
*Natural flowering season.*—Summer to late summer (July to September).
*Height.*—9.9 cm.
*Width.*—8.9 cm.
*Fragrance.*—Moderate, sweet; typical *Plox paniculata* scent.
*Flower number* (*per inflorescence*).—40.
*Quantity of flowers per lateral stem.*—10.
*Quantity of flower buds per lateral stem.*—30.
*Quantity of flower and buds per plant.*—160.
*Rate of flower opening.*—Approximately 25% of the flowers at any stage.
*Flower longevity on plant.*—10 days.
*Flower longevity as a cut flower.*—10 days.

Peduncle:
*Color.*—Between RHS 144A (Yellow-green) to RHS 144B (Yellow-green).
*Length.*—Primary: 6.8 cm. Secondary: 2.7 cm.
*Diameter.*—Primary: 0.2 cm. Secondary: 0.1 cm.
*Angle.*—Primary peduncles have an average angle of 0° (straight upright), secondary peduncles have an average angle of 35° C.
*Strength.*—Strong.

Pedicel:
*Color.*—Between RHS 144A (Yellow-green) to RHS 144B (Yellow-green).
*Length.*—0.5 cm.
*Diameter.*—0.1 cm.
*Angle.*—Average angle 30° (0° to 60°) (0° equals straight on top of the peduncle).
*Strength.*—Strong.

Florets:
*Type.*—Single.
*Shape.*—Salverform.
*Aspect.*—Upright and outward.
*Fragrance.*—Moderate, sweet; typical *Phlox paniculata* scent.
*Size.*—Height (flower depth): 2.8 cm. Diameter: 3.4 cm.
*Petals.*—Arrangement: Rotate. Shape: Spathulate, the lower 60% fused into a tube. Appearance: Dull, smooth. Number: 5, fused into a tube (lower 60% of each petal). Size: Length: 3.7 cm (lower 2.2 cm fused into a tube). Width: 2.1 cm. Apex: Rounded. Margin: Entire. Color (when opening): Upper surface: RHS 155C (White), base of free part RHS 157C (Green-white), tube RHS 157D (Green-white). Lower surface: RHS 155C (White), tube RHS 157B (Green-white). Color (fully opened): Upper surface: Slightly whiter than RHS 155C (White), base of free part between RHS 157C (Green-white) to RHS 157D (Green-white), tube RHS 157D (Green-white). Lower surface: RHS 155C (White), tube RHS 157D (Green-white). Texture (both surfaces): Smooth.

Calyx:
*Shape.*—Campanulate.
*Length.*—1.2 cm.
*Diameter.*—0.4 cm.
*Sepals.*—Arrangement: Rotate. Appearance: Smooth, dull. Number: 5. Shape: Linear. Apex: Narrow apiculate. Base: Lower 55% fused. Margin: Entire. Size: Length: 1.2 cm. Width: 0.2 cm. Color (mature): Upper surface: RHS 144B (Yellow-green); tips slightly flushed RHS 200A (Brown). Lower surface: RHS 144B (Yellow-green); tips slightly flushed RHS 200A (Brown). Color (immature): Upper surface: RHS 144A (Yellow-green); base RHS 144C. Lower surface: RHS 144A (Yellow-green); base RHS 144C.

Reproductive organs:
*Stamens.*—Quantity: 5. Anther: Shape: Basifixed, oblong; filament implanted in petal. Length: 0.3 cm. Length of filament: 0.1 cm. Color: RHS 4D (Yellow).
*Pollen.*—Amount: Moderate. Color: RHS 4C (Yellow).
*Pistil.*—Quantity: 1. Length: 1.8 cm.
*Style.*—Length: 1.7 cm. Color: RHS 150D (Yellow-green).
*Stigma.*—Shape: Cleft (3-parted). Color: Between RHS 150C (Yellow-green) to RHS 150D (Yellow-green).
*Ovary color.*—RHS 143A (Green).

Fruit and Seed Set: No fruit or seeds have been detected to date.

Disease and insect resistance: No particular resistance or susceptibility to diseases or insects noted to date.

COMPARISON WITH COMMERCIAL CULTIVARS

'Pina Colada' differs from the commercial *Phlox paniculata* variety 'David' (unpatented), by being a more sturdy plant with healthier foliage and thicker stems than 'David'.

Additionally, 'Pina Colada' has a more compact plant habit and flowers that are more evenly distributed and richer than 'David'.

'Pina Colada' differs from the commercial *Phlox* variety 'Grenadine Dream' (U.S. Plant patent application No. 11/1725,797), by having pure white flowers while 'Grenadine Dream' has rich red-purple flowers.

I claim:

1. A new and distinct cultivar of *phlox* plant as shown and described herein.

* * * * *